(12) United States Patent
Ma et al.

(10) Patent No.: US 6,559,354 B1
(45) Date of Patent: May 6, 2003

(54) TRANSCRIPTION AND GENE EXPRESSION REGULATORS

(75) Inventors: Hongchang Ma, Newark, DE (US); Omolayo O. Famodu nee Morakinyo, Newark, DE (US); Joan T. Odell, Unionville, PA (US); Emil M. Orozco, Jr., West Grove, PA (US); J. Antoni Rafalski, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 72 days.

(21) Appl. No.: 09/699,266

(22) Filed: Oct. 27, 2000

Related U.S. Application Data

(63) Continuation of application No. PCT/US99/08385, filed on Apr. 16, 1999.
(60) Provisional application No. 60/083,212, filed on Apr. 27, 1998.

(51) Int. Cl.$^7$ .......................... C12N 15/87; C12N 5/02; A01H 11/00; C07H 21/04
(52) U.S. Cl. ...................... 800/278; 800/295; 435/410; 536/23.6
(58) Field of Search ............................... 536/23.1, 23.6; 435/69.1, 320.1, 325, 252.3, 410; 800/278, 295

(56) References Cited

U.S. PATENT DOCUMENTS

| | | |
|---|---|---|
| 5,231,020 A | 7/1993 | Jorgensen et al. |
| 6,239,327 B1 | 5/2001 | Grossniklaus et al. |

OTHER PUBLICATIONS

Siyuan Le et al., Yeast, vol. 13:1029–1042, 1997, Two new S–Phase–Speicific Genes from *Saccharomyces cerevisiae*.
EMBL Sequence Library Database Accession No.: AA624789, Oct. 16, 1997, Marra et al., The WashU–HHMI Mouse EST Project.
Justin Goodrich et al., Nature, vol. 386(386):44–51, 1997, A polycomb–group gene regulates homeotic gene expression in Arabidopsis.
EMBL Sequence Library Database Accession No.: O04246, Jul. 1, 1997, Johnson et al., Putative curly leaf–like 1 homeotic protein.
EMBL Sequence Library Database Accession No.: AQ273801, Nov. 4, 1998, Yu et al., A BAC end sequencing framework to sequence the rice genome.
Renato Paro et al., Trends in Genetics, vol. 6:416–421, 1990, Imprinting a determined state into the chromatin of Drosophila.
Detlef Weigel, Curr. Biol., vol. 7:R373–R375, Flower development: Repressing reproduction.
Nir Ohad et al., Plant Cell, vol. 11:407–416, 1999, Mutations in FIE, a WD Polycomb Group Gene, Allow endosperm Development without Fertilization.
National Center for Biotechnology Information General Identifier No. L07593, Sep. 10, 1997, Le, S. et al., Two New S–Phase–Speicific Genes from *Saccharomyces cerevisiae*.
National Center for Biotechnology Information General Identifer No. 171091, Sep. 10, 1997, Le, S. et al., Two new S–Phase–Specific Genes from *Saccharomyces cerevisiae*.
National Center for Biotechnology Information General Indentifier No. 416657, Oct. 1, 2000, Le, S. Two new S–Phase–Speicific Genes from *Saccharomyces cerevisiae*.
Celina Cziepluch et al., Yeast, vol. 12:1471–1474, 1996, Sequencing analysis of a 40*2 kb Fragment of yeast chrosome X reveals 19 Open Reading Frames including URA2 (5' end), TRK1, PBS2, SPT10, GCD14, RPE1, PHO86, NCA3, ASF1, CCT7, GZF3, two tRNA genes, three remnant Delta Elements and a Ty4 Transposon.
National Center for Biotechnology Information General Identifier No. 1903018, Mar. 18, 1997, Goodrich, J. et al., A polycomb–group gene regulates homeotic gene expression in Arabidopsis.
National Center for Biotechnology Information General Identifier No. 1903019, Goodrich, J. et al., A polycomb–group gene regulates homeotic gene expression in Arabidopsis.
National Center for Biotechnology Information General Identifier No. 3242729, Apr. 5, 2000, Lin, X. et al., Sequence and analysis of chromosome 2 of the plant *Arabidopsis thaliana*.
Xiaoying Lin et al., Nature, vol. 402:761–768, 1999, Sequence and analysis of chromosome 2 of the plant *Arabidopsis thaliana*.
National Center for Biotechnology Information General Identifier No. 4185507, Jan. 25, 1999, Bilodeau, P. et al.

*Primary Examiner*—Karen Cochrane Carlson

(57) ABSTRACT

This invention relates to an isolated nucleic acid fragment encoding a transcription or gene expression regulator. The invention also relates to the construction of a chimeric gene encoding all or a portion of the transcription or gene expression regulator, in sense or antisense orientation, wherein expression of the chimeric gene results in production of altered levels of the transcription or gene expression regulator in a transformed host cell.

13 Claims, 8 Drawing Sheets

```
SEQ ID NO:7    MSIVSLLGIKVLNNPAKFTDPYEFEITFECLESLKHDLEWKLTYVGSSRSLDHDQELDSI
SEQ ID NO:2    MSAVNITNVAVLDNPTAFLNPFQFEISYECLVPLDDDLEWKLIYVGSAEDENYDQQLESV
SEQ ID NO:4    MSVVSLLGVTVRNNPAKFVDPYEFEITFECLEALQKDLEWKLTYVGSATSDEHDQELDSL
SEQ ID NO:6    MSVVSLLGVNVLQNPARFGDPYEFEITFECLETLQKDLEWKLTYVGSATSNDHDQELDSL
               1                                                          60

SEQ ID NO:7    LVGPVPVGVNKFVFSADPPSAELIPASELVSVTVILLSCSYDGREFVRVGYYVNNEYDEE
SEQ ID NO:2    LVGPVNVGTYRFVLQADPPDPSKIREEDIIGVTVLLLTCSYMGQEFMRVGYYVNNDYDDE
SEQ ID NO:4    LVGPIPVGVNKFLFQADAPDTKRIPXXEILGVTVILLTCAYDGKEFVRVGYYVNNEYDSE
SEQ ID NO:6    LVGPIPVGVNKFIFVADPPDTNKIPDAEILGVTVILLTCAYDGREFFRVGYYVNNEYDSD
               61                                                        120

SEQ ID NO:7    ELRENPPAKVQVDHIVRNILAEKPRVTRFNIVWDNENEGD-LYPPEQPGVDDEEEEDDEE
SEQ ID NO:2    QLREEPPAKVLIDRVQRNILADKPRVTKFPI-----------------------------
SEQ ID NO:4    EL----------------------------------------------------------
SEQ ID NO:6    ELNTDPPAKPILEKVRRNILAEKPRVTRFAIKWDSDDSAPPLYPPEQPEADLVADGEEYG
               121                                                       180
```

FIG. 1A

```
SEQ ID NO:7    EDDDEDDEDDEDDDQEDGEGEAEEAAEEEEEEKTEDNETNLEEEEDIENSDGDEEG
SEQ ID NO:2    --------------------------------------------------------
SEQ ID NO:4    --------------------------------------------------------
SEQ ID NO:6    AEEAEDEDEEESADGPEVPADPDVMIDDSEAAGAMVETVKATEEESDAGSEDLEAESSGS
                181                                                      240

SEQ ID NO:7    EEEVGSVDKNEDGNDKKRRKIEGGSTDIESTPKDAARSTN
SEQ ID NO:2    ----------------------------------------
SEQ ID NO:4    ----------------------------------------
SEQ ID NO:6    EE--------------------------------------
                241                                  280
```

FIG. 1B

```
SEQ ID NO:12                                                   MASEASPSSSATRSEPPKDSPAEERGPASKEVSE------VIESLKKKLAADRCISI    60
SEQ ID NO:09   VASSASASASAGRSRPSSSAAQVTSNSAVRAGEENAASLYVLSVIDSLKKRITADRLTYI
               1

SEQ ID NO:12   KKRIDENKKNLFAITQSFMRSSMERGGSCKDGSD----LLVKRQRDS----PGMKSGIDE   120
SEQ ID NO:09   KNRIGENKTNISSYTQRTYNLSKNRQISTSKGTDSASNLLTKRQDDALCTLHSLDIIPVD
               61

SEQ ID NO:12   SNNNRYVEDGP--ASSGMVQGSSVPVKISLRPIKMPDIKRLSPYTTWVFLDRNQRMTEDQ   180
SEQ ID NO:09   KDGGTFQDESPFSSSNVMFGGNLGPKNAIIRPIKLPEVPKLPPYTTWIFLDRNQRMTEDQ
               121

SEQ ID NO:12   SVVGRRRIYYDQTGGEALICSDSEEEAIDEEEKRDFLEPEDYIIRMTLEQLGLSDSVLA    240
SEQ ID NO:09   SVLGRRRIYYDTSCGEALICSDSEDEAIEDEEEKKEFKHSEDHIIRMTVQECGMSDAVLQ
               181

SEQ ID NO:12   ELASFLSRSTSEIKARHGVLM--KEKEVSESGDNQA---ESSLLNKDMEGALDSFDNLFC   300
SEQ ID NO:09   TLARHMERAADDIKARYEILHGEKTKDSCKKGTEHNVKVEDLYCDKDLDAALDSFDNLFC
               241
```

FIG. 2A

```
SEQ ID NO:12    R----RCLVFDCRLHGCSQDLIFPAEKPAPWCPPVDENLTCGANCYKTLLKSGRFPGYGT
SEQ ID NO:09    RPREQRCLVFDCKLHGCSQDLVFPTEKQPAW-SGVDDSVPCGIHCHKLASEPDAAAGADH
                301                                                       360

SEQ ID NO:12    I---EGKTGTSSDGAGTKTTPTKFSSKLNGRKPKTFPSESASSNEKCALETSDSENGLQQ
SEQ ID NO:09    MLFDVEEPTHSSDNVMNQPGSNRKKNGSSGRKTKSQQSESSSTA-RVISESSDSEVHPIS
                361                                                       420

SEQ ID NO:12    DTNSDKVSSSPKVKGSGRRVGRKRNKNRVAERVPRKTQKRQKKTEASDSDSIASGSCSPS
SEQ ID NO:09    NKSPQHSPSPSKVKIGPKGGIRKITNRRIAERILMSVKKGQREMASSDSNFV-SGYLLAR
                421                                                       480

SEQ ID NO:12    DAKHKDNEDATSSSQKHV------KSGNSGKSRKNGTPAEVSNNSVKDDVPVCQSNEVASE
SEQ ID NO:09    DMKLRSD---TRNGNKELIVSSQQSSPSTRSSKKKSTPQIGNSSAFAEAHNDSTEEANNR
                481                                                       540

SEQ ID NO:12    LDAPGSDESLRKEEFMGETVSRGRLATNKLWRPLEKSLFDKGVEIFGMNSCLIARNLLSG
SEQ ID NO:09    HSATDGYDSSRKEEFVNENLCKQEVYLRS-WKAIEQGLLVKGLEIFGRNSCLIARNLLGG
                541                                                       600
```

FIG. 2B

```
SEQ ID NO:12   FKSCWEVFQYMTCSENKASFFGGDGLNPDGSSKFDINGNMVNNQVRRRSRFLRRRGKVRR
SEQ ID NO:09   MKTCKDVFQYMNYIENNSA----SGALSGVDSL---VKGYIKGTELRTRSRYFRRRGKVRR
                                                                          660
               601

SEQ ID NO:12   LKYTWKSAAYHSIRKRITEKKDQPCRQFNPCNCKIACGKECPCLLNGTCCEKYCGCPKSC
SEQ ID NO:09   LKYTWKSAGYNF--KRITERKDQPCRQYNPCGCQSTCGKQCPCLSNGTCCEKYCGCPKIC
                                                                          720
               661

SEQ ID NO:12   KNRFRGCHCAKSQCRSRQCPCFAADRECDPDVCRNCWVIGGDGSLGVPSQRGDNYECRNM
SEQ ID NO:09   KNRFRGCHCAKSQCRSRQCPCFAADRECDPDVCRNCWGCGDGTLGVPNQRGDNYECRNM
                                                                          780
               721

SEQ ID NO:12   KLLLKQQQRVLLGISDVSGWGAFLKNSVSKHEYLGEYTGELISHKEADKRGKIYDRENCS
SEQ ID NO:09   KLLLKQQQRVLLGRSDVSGWGAFLKNSVSKHEYLGEYTGELISHKEADKRGKIYDRENSS
                                                                          840
               781

SEQ ID NO:12   FLFNLNDQFVLDAYRKGDKLKFANHSPEPNCYAKVIMVAGDHRVGIFAKERILAGEELFY
SEQ ID NO:09   FLFNLNNEYVLDAYRMGDKLKFANHAPDPNCYAKVIMVTGDHRVGIFAKERILAGEELFY
                                                                          900
               841

FIG. 2C
```

SEQ ID NO:12  DYRYEPDRAPAWAKKPEAPGSKKDENVTPSVGRPKKLA
SEQ ID NO:09  DYRYEPDRAPAWARKPEASGAKDDGQ--PFNGRAKKLA
              901                                  938

FIG. 2D

```
SEQ ID NO:13   490  STEWNPIEKDLYLKGVEIFGRNSCLIARNLLSGLKTCLDVSNYMRENEVSVFRRSSTPNL  549
SEQ ID NO:11        S-HWSTLERDLYLKGIEIFGKNSCLIVRNLLCGLKTCMEVASYMYNNGAANMSKSISGDF

SEQ ID NO:13   550  LLDDGRTDPGNDNDEVPPRTRLFRRKGKTRKLKYSTKSAGHPSVWKRIAGGKNQSC-KQY  609
SEQ ID NO:11        ----TETEQNYMEQGMVVRTKVCRRRGRTRKHKYPSKAAGHPAIRKKVGDGKQ--CDRQY

SEQ ID NO:13   610  TPCGCLSMCGKDCPCLTNETCCEKYCGCSKSCKNRFRGCHCAKSQCRSRQCPCFAAGREC  669
SEQ ID NO:11        TPCGCQEMCNKNCPCVENGTCCEKYCGCSKSCKNRFRGCHCAKISAEAGNAHVLLPSGNV

SEQ ID NO:13   670  DPDVCRNCWVSCGDGSL-GEAPRRGE------GQCGNMRLLLRQQQRILLGKSDVAGWGA  722
SEQ ID NO:11        IRMFCRNCW------GELWSGSPRRATKKEVMVTQCGNMKLLLKQQQRILLGKSDVAGWGA

SEQ ID NO:13   723  FLKNSVSKNEYLGEYTGELISHHEADKRGKIYDRANSSFLFDLNDQYVLDAQRKGDKLKF  782
SEQ ID NO:11        FIKNPVHKNDYLGEYTGELISHKEADKRGKIYDRANSSFLFDLNDQFVLDAYRKGDKLKF

SEQ ID NO:13   783  ANHSAKPNCYAKVMFVAGDHRVGIFANERIEASEELFYDYRYGPDQAPVWARKPEGSKKD  842
SEQ ID NO:11        ANHSSSPNCYAKVMMVAGDHRVGIYAREHIEASAELFYDYRYGPDQAPAWARRPEGAKKD
```

FIG. 3A

```
SEQ ID NO:13   843  DSAITHRRARKHQSH  857
SEQ ID NO:11        EASGSHRRAHK----
```

FIG. 3B

US 6,559,354 B1

TRANSCRIPTION AND GENE EXPRESSION REGULATORS

CROSS-REFERENCE TO RELATED APPLICATIONS

This application is a continuation of International Application No. PCT/US99/08385 filed Apr. 16, 1999, now pending, which claims priority benefit of U.S. Provisional Application No. 60/083,212 filed Apr. 27, 1998.

FIELD OF THE INVENTION

This invention is in the field of plant molecular biology. More specifically, this invention pertains to nucleic acid fragments encoding factors involved in regulation of transcription and gene expression in plants and seeds.

BACKGROUND OF THE INVENTION

Factors involved in the control of gene expression are important throughout plant development. Anti-silencing function genes have been described for the budding yeast *Saccharomyces cerevisiae*. Overexpression of anti-silencing function genes leads to derepression of the silent mating type loci. At least two genes encode anti-silencing proteins which in yeast have been ascribed the designation ASF1 and ASF2, for anti-silencing function 1 and 2, respectively. Anti-silencing function genes are transcribed in a cell-cycle-specific manner and at least one of them is suggested to play a role in DNA repair and chromosome maintenance (Davis, L. S., Konopka, J. B. and Sternglanz, R. (1997) *Yeast* 13:1029–1042). There is no prior description of these functions or their genes in plants.

The fate of plant cells is position dependent and maintained through interactions between neighboring cells. Polycomb-group genes are involved in the maintenance of fate in *Drosophila melanogaster*. (Paro, R. (1990) *Trends Genet.* 6:416–421). Polycomb group-like proteins have been identified in *Arabidopsis thaliana* where they have been shown to be necessary for the stable repression of a floral homeotic gene and to promote fate determination (Goodrich, J. et al. (1997) *Nature* 386:44–51; Weigel D. (1997) *Curr. Biol.* 7:R373–R375). While a family of polycomb-like proteins have been identified in insects and animals, not all of the different classes have been identified in plants. Polycomb group proteins are thought to assemble in a nuclear complex and to play a major role in endosperml development and fertilization (Ohad, N. et al. (1999) *Plant Cell* 11:407–416). Polycomb-group genes have not been previously described in monocots.

SUMMARY OF THE INVENTION

The instant invention relates to isolated nucleic acid fragments encoding factors involved in regulation of gene expression. Specifically, this invention concerns an isolated nucleic acid fragment encoding an anti-silencing protein or a polycomb-group protein. In addition, this invention relates to a nucleic acid fragment that is complementary to the nucleic acid fragment encoding an anti-silencing protein or a polycomb-group protein.

An additional embodiment of the instant invention pertains to a polypeptide encoding all or a substantial portion of a factor involved in regulation of transcription or gene expression selected from the group consisting of anti-silencing proteins and polycomb-group proteins.

In another embodiment, the instant invention relates to a chimeric gene encoding an anti-silencing protein or a polycomb-group protein, or to a chimeric gene that comprises a nucleic acid fragment that is complementary to a nucleic acid fragment encoding an anti-silencing protein or a polycomb-group protein, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding an anti-silencing protein or a polycomb-group protein, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of an anti-silencing protein or a polycomb-group protein in a transformed host cell comprising: a) transforming a host cell with a chimeric gene comprising a nucleic acid fragment encoding an anti-silencing protein or a polycomb-group protein; and b) growing the transformed host cell under conditions that are suitable for expression of the chimeric gene wherein expression of the chimeric gene results in production of altered levels of an anti-silencing protein or a polycomb-group protein in the transformed host cell.

An addition embodiment of the instant invention concerns a method for obtaining a nucleic acid fragment encoding all or a substantial portion of an amino acid sequence encoding an anti-silencing protein or a polycomb-group protein.

BRIEF DESCRIPTION OF THE DRAWINGS AND SEQUENCE DESCRIPTIONS

The invention can be more fully understood from the following detailed description and the accompanying drawings and Sequence Listing which form a part of this application.

FIGS. 1A and 1B depicts the amino acid sequence alignment between the anti-silencing proteins from corn clone crln.pk0184.h11 (SEQ ID NO:2), soybean clone sls2c.pk018.k22 (SEQ ID NO:4), wheat clone wlm96.pk0014.a10 (SEQ ID NO:6) and *Saccharomyces cerevisiae* (NCBI General Identifier No. 416657, SEQ ID NO:7). Dashes are used by the program to maximize alignment of the sequences.

FIGS. 2A, 2B, 2C, and 2D depicts the amino acid sequence alignment between the polycomb group proteins from corn clone ccl.pk0026.c11 (SEQ ID NO:9) and *Arabidopsis thaliana* (NCBI General Identifier No. 3242729, SEQ ID NO:12). Dashes are used by the program to maximize alignment of the sequences.

FIGS. 3A and 3B depicts the amino acid sequence alignment between the polycomb group proteins from wheat clone wdrl.pk0002.e12 (SEQ ID NO:11) and *Arabidopsis thaliana* amino acids 490 through 857 (NCBI General Identifier No.4185507, SEQ ID NO:13). Numbering above the alignment indicates the amino acid location in SEQ ID NO:11. Dashes are used by the program to maximize alignment of the sequences.

The following sequence descriptions and Sequence Listing attached hereto comply with the rules governing nucleotide and/or amino acid sequence disclosures in patent applications as set forth in 37 C.F.R. §1.821–1.825.

SEQ ID NO:1 is the nucleotide sequence comprising the entire cDNA insert in clone crln.pk0184.h11 encoding a corn anti-silencing protein.

SEQ ID NO:2 is the deduced amino acid sequence of a corn anti-silencing protein derived from the nucleotide sequence of SEQ ID NO:1.

SEQ ID NO:3 is the nucleotide sequence comprising a portion of the cDNA insert in clone sls2c.pk018.k22 encoding a substantial portion of a soybean anti-silencing protein.

SEQ ID NO:4 is the deduced amino acid sequence of a substantial portion of a soybean anti-silencing protein derived from the nucleotide sequence of SEQ ID NO:3.

SEQ ID NO:5 is the nucleotide sequence comprising the entire cDNA insert in clone wlm96.pk0014.a10 encoding an entire wheat anti-silencing protein.

SEQ ID NO:6 is the deduced amino acid sequence of an entire wheat anti-silencing protein derived from the nucleotide sequence of SEQ ID NO:5.

SEQ ID NO:7 is the amino acid sequence of a *Saccharomyces cerevisiae* anti-silencing protein having an NCBI General Identifier No. 416657.

SEQ ID NO:8 is the nucleotide sequence comprising the entire cDNA insert in clone: ccl.pk0026.c11 encoding an entire corn polycomb group protein.

SEQ ID NO:9 is the deduced amino acid sequence of an entire corn polycomb group protein derived from the nucleotide sequence of SEQ ID NO:8.

SEQ ID NO:10 is the nucleotide sequence comprising a portion of the cDNA insert in clone wdrl.pk0002.e12 encoding the C-terminal half of a wheat polycomb group protein.

SEQ ID NO:11 is the deduced amino acid sequence of the C-terminal half of a wheat polycomb group protein derived from the nucleotide sequence of SEQ ID NO:10.

SEQ ID NO:12 is the amino acid sequence of a *Arabidopsis thaliana* polycomb group protein having an NCBI general identifier No. 3242729.

SEQ ID NO:13 is the sequence of amino acids 490 through 856 of a *Arabidopsis thaliana* polycomb group protein having an NCBI general identifier No. 4185507.

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, the term "isolated polynucleotide refers to a polynucleotide that is substantially free from other nucleic acid sequences, such as other chromosomal and extrachromosomal DNA and RNA that normally accompany or interact with the isolated polynucleotide as found in its naturally occurring environment. An isolated nucleic acid fragment in the form of a polymer of DNA may be comprised of one or more segments of cDNA, genomic DNA or synthetic DNA.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a gene which result in the production of a chemically equivalent amino acid at a given site, but do not affect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, substantially similar nucleic acid fragments may also be characterized by their ability to hybridize, under stringent conditions (0.1×SSC, 0.1% SDS, 65° C.), with the nucleic acid fragments disclosed herein.

Substantially similar nucleic acid fragments of the instant invention may also be characterized by the percent similarity of the amino acid sequences that they encode to the amino acid sequences disclosed herein, as determined by algorithms commonly employed by those skilled in this art. Preferred are those nucleic acid fragments whose nucleotide sequences encode amino acid sequences that are 80% similar to the amino acid sequences reported herein. More preferred nucleic acid fragments encode amino acid sequences that are 90% similar to the amino acid sequences reported herein. Most preferred are nucleic acid fragments that encode amino acid sequences that are 95% similar to the amino acid sequences reported herein. Sequence alignments and percent similarity calculations were performed using the Megalign program of the LASARGENE bioinformatics computing suite (DNASTAR Inc., Madison, Wis.). Multiple alignment of the sequences was performed using the Clustal method of alignment (Higgins, D. G. and Sharp, P. M. (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403–410). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to afford specific identification and/or isolation of a nucleic acid fragment comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the anti-silencing protein or polycomb group proteins as set forth in SEQ ID NOs:2, 4, 6, 9 and 11. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1–82. It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065, incorporated herein by reference). The complementarity of an antisense RNA may be with any part of the specific gene transcript, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels, J. J., (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1 987) *Meth. Enzymol.* 143:277) and particle-accelerated or "gene gun" transformation technology (Klein T. M. et al. (1987) *Nature (London)* 327:70–73; U.S. Pat. No. 4,945,050, incorporated herein by reference).

Standard recombinant DNA and molecular cloning techniques used herein are well known in the art and are described more fully in Sambrook, J., Fritsch, E. F. and Maniatis, T. *Molecular Cloning: A Laboratory Manual;* Cold Spring Harbor Laboratory Press: Cold Spring Harbor, 1989 (hereinafter "Maniatis").

Nucleic acid fragments encoding at least a portion of several transcription and gene expression regulators have been isolated and identified by comparison of random plant cDNA sequences to public databases containing nucleotide and protein sequences using the BLAST algorithms well known to those skilled in the art. Table 1 lists the proteins that are described herein, and the designation of the cDNA clones that comprise the nucleic acid fragments encoding these proteins.

TABLE 1

Transcription and Gene Expression Regulators

| Enzyme | Clone | Plant |
|---|---|---|
| Anti-silencing protein | cr1n.pk0184.h11 | Corn |
| | s1s2c.pk018.k22 | Soybean |
| | w1m96.pk0014.a10 | Wheat |
| Polycomb group protein | cc1.pk0026.c11 | Corn |
| | wdr1.pk0002.e12 | Wheat |

The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other anti-silencing proteins or polycomb group proteins, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer. is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al., (1988) *Proc. Natl. Acad Sci. USA* 85:8998) to generate; cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., (1989) *Proc. Natl. Acad. Sci. USA* 86:5673; Loh et al., (1989) *Science* 243:217). Products generated by the 3' and 5' RACE procedures can be combined to generate full-length cDNAs (Frohman, M. A. and Martin, G. R., (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. (1984) *Adv. Immunol.* 36:1; Maniatis).

The nucleic acid fragments of the instant invention may be used to create transgenic plants in which the disclosed anti-silencing protein or polycomb group protein are present at higher or lower levels than normal or in cell types or developmental stages in which they are not normally found. This would have the effect of altering the level of cosuppression and/or gene silencing in those cells. Polycomb-group proteins are involved in maintenance of the heterochromatin structure and consequently inactivating gene function. It may thus be possible to suppress cosupression by downregulating the polycomb-group proteins, or to enhance cosupression by upregulating them. Anti-silencing proteins are expressed at specific stages of the cell cycle. Over- or under-expression of these proteins may lead to changes in fate determination at different stages of the cell cycle.

Overexpression of the anti-silencing protein or polycomb group proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

It may also be desirable to reduce or eliminate expression of genes encoding anti-silencing protein or polycomb group protein in plants for some applications. In order to accomplish this, a chimeric gene designed for co-suppression of the instant transcription and gene expression regulators can be constructed by linking a gene or gene fragment encoding an anti-silencing protein or a polycomb group protein to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

The instant anti-silencing protein or polycomb group protein (or portions thereof) may be produced in heterologous host cells, particularly in the cells of microbial hosts, and can be used to prepare antibodies to the these proteins by methods well known to those skilled in the art. The antibodies are useful for detecting anti-silencing protein or polycomb group protein in situ in cells or in vitro in cell extracts. Preferred heterologous host cells for production of the instant anti-silencing protein or polycomb group protein are microbial hosts. Microbial expression systems and expression vectors containing regulatory sequences, that direct high level expression of foreign proteins are well known to those skilled in the art. Any of these could be used to construct a chimeric gene for production of the instant anti-silencing protein or polycomb group protein. This chimeric gene could then be introduced into appropriate microorganisms via transformation to provide high level expression of the encoded transcription and gene expression regulators. An example of a vector for high level expression of the instant anti-silencing protein or polycomb group protein in a bacterial host is provided (Example 7).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et at., (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein, D. et al., (1980) *Am. J. Hum. Genet.* 32:314–331).

The production and use of plant gene-derived probes for use in genetic mapping is described in R. Bernatzky, R. and Tanksley, S. D. (1986) *Plant Mol. Biol. Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used: for physical mapping (i.e., placement of sequences on physical maps; see Hoheisel, J. D., et al., In: *Nonmammalian Genomic Analysis: A Practical Guide,* Academic press 1996, pp. 319–346, and references cited therein).

In another embodiment, nucleic acid probes derived from the instant nucleic acid sequences may be used in direct fluorescence in situ hybridization (FISH) mapping (Trask, B. J. (1991) *Trends Genet.* 7:149–154). Although current methods of FISH mapping favor use of large clones (several to several hundred KB; see Laan, M. et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian, H. H. (1989) *J. Lab. Clin. Med.* 114(2):95–96), polymorphism of PCR-amplified fragments (CAPS; Sheffield, V. C. et al. (1993) *Genomics* 16:325–332), allele-specific ligation (Landegren, U. et al. (1988) *Science* 241:1077–1080), nucleotide extension reactions (Sokolov, B. P. (1 990) *Nucleic Acid Res.* 18:3671), Radiation Hybrid Mapping (Walter, M. A. et al. (1997) *Nature Genetics* 7:22–28) and Happy Mapping (Dear, P. H. and Cook, P. R. (1989) *Nucleic Acid Res.* 1 7:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer, (1989) *Proc. Natl. Acad. Sci USA* 86:9402; Koes et al., (1995) *Proc. Natl. Acad Sci USA* 92:8149; Bensen et al., (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the anti-silencing protein or the polycomb group protein. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding an anti-silencing protein or a polycomb group protein can be identified and obtained. This mutant plant can then be used to determine or confirm the natural function of the anti-silencing protein or the polycomb group protein product.

EXAMPLES

The present invention is further defined in the following Examples, in which all parts, and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries: Isolation and Sequencing of cDNA Clones cDNA libraries representing mRNAs from various corn, soybean and wheat tissues were prepared. The characteristics of the libraries are described below.

TABLE 2 cDNA Libraries from Corn, Soybean and Wheat

| Library | Tissue | Clone |
| --- | --- | --- |
| cc1 | Corn Undifferentiated Callus | cc1.pk0026.c11 |
| cr1n | Corn Root From 7 Day Old Seedlings* | cr1n.pk0184.h11 |
| sls2c | Soybean Infected With *Sclerotinia sclerotiorum* mycelium | sls2c.pk018.k22 |
| wdr1 | Wheat Developing Root and Leaf | wdr1.pk0002.e12 |
| wlm96 | Wheat Seedlings 96 Hours After Inoculation With *Erysiphe graminis* f. sp *tritici* | wlm96.pk0014.a10 |

*This library was normalized essentially as described in U.S. Pat. No. 5,482,845 cDNA libraries were prepared in Uni-ZAP™ XR vectors according to the manufacturer's protocol (Stratagene Cloning Systems, La Jolla, Calif.). Conversion of the Uni-ZAP™ XR libraries into plasmid libraries was accomplished according to the protocol provided by Stratagene. Upon conversion, cDNA inserts were contained in the plasmid vector pBluescript. cDNA inserts from randomly picked bacterial colonies containing recombinant pBluescript plasmids were amplified via polymerase chain reaction using primers specific for vector sequences flanking the inserted cDNA sequences or plasmid DNA was prepared from cultured bacterial cells. Amplified insert DNAs or plasmid DNAs were sequenced in dye-primer sequencing reactions to generate partial cDNA sequences (expressed sequence tags or "ESTs"; see Adams, M. D. et al., (1991) *Science* 252:1651). The resulting ESTs were analyzed using a Perkin Elmer Model 377 fluorescent sequencer.

Example 2

Identification of cDNA Clones

ESTs encoding transcription and gene expression regulators were identified by conducting BLAST (Basic Local Alignment Search Tool; Altschul, S. F., et al., (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST: "hit" represent homologous proteins.

Example 3

Characterization of cDNA Clones Encoding Anti-Silencinz Protein

The BLASTX search using the EST sequences from clones crln.pk0057.b4, wlm96.pk0014.a10, and a contig assembled from clones crln.pk0096.b1, cebl.pk0050.h8, crln.pk0148.g3 and crln.pk0184.h11 revealed similarity of the proteins encoded by the cDNAs to yeast anti-silencing function protein (ASFI) from *Saccharomyces cerevisiae* (GenBank Accession No. L07593, NCBI General Identifier No. 171091). The BLAST results for each of these sequences are shown in Table 3:

TABLE 3

BLAST Results for Clones Encoding Polypeptides Homologous to Anti-Silencing Function Protein

| Clone | BLAST pLog Score GenBank Accession No. L07593 |
|---|---|
| crln.pk0057.b4 | 11.48 |
| Contig of clones: | 29.13 |
| crln.pk0096.b1 | |
| cebl.pk0050.h8 | |
| crln.pk0148.g3 | |
| crln.pk0184.h11 | |
| wlm96.pk0014.a10 | 47.36 |

The sequence of the entire cDNA insert in clone crln.pk0184.h11 was determined and is shown in SEQ ID NO:1; the deduced amino acid sequence of this cDNA is shown in SEQ ID NO:2. The amino acid sequence set forth in SEQ ID NO:2 was evaluated by BLASTP, yielding a pLog value of 48.1 versus the *Saccharomyces cerevisiae* anti-silencing protein 1 sequence (NCBI General Identifier No. 416657). The sequence of the entire cDNA insert in clone crln.pk0096.b1 was determined and found to be identical to the nucleotide sequence set forth in SEQ ID NO:1, both of these sequences encode 151 amino acids suggesting that corn produces a monofunctional protein. The sequence of the entire cDNA insert in clone wlm96.pk0004.a10 was determined and is shown in SEQ ID NO:5; the deduced amino acid sequence of this cDNA is shown in SEQ ID NO:7. The amino acid sequence set forth in SEQ ID NO:7 was evaluated by BLASTP, yielding a pLog value of 73.3 versus the *Saccharomyces cerevisiae* anti-silencing protein 1 sequence (NCBI General Identifier No. 416657).

TBLASTN analysis of the proprietary plant EST database indicated that a soybean clone (sls2c.pk018.k22) also encoded anti-silencing protein 1. The BLASTX search using the EST sequences from clone sls2c.pk018.k22 revealed similarity of the proteins encoded by the cDNAs to anti-silencing protein 1 from *Saccharomyces cerevisiae* (NCBI General Identifier No. 416657) with a pLog value of 45.52.

FIGS. 1A and 1B presents an alignment of the amino acid sequences set forth in SEQ ID NOs:2, 4 and 6 and the *Saccharomyces cerevisiae* sequence (NCBI General Identifier No. 416657; SEQ ID NO:7). The data in Table 4 represents a calculation of the percent similarity of the amino acid sequences set forth in SEQ ID NOs:2, 4 and 6 and the *Saccharomyces cerevisiae* anti-silencing protein 1 sequence.

TABLE 4

Percent Similarity of Amino Acid Sequences Deduced From the Nucleotide Sequences of cDNA Clones Encoding Polypeptides Homologous to Anti-Silencing Protein 1

| Clone | SEQ ID NO. | Percent Similarity to 416657 |
|---|---|---|
| crln.pk0184.h11 | 2 | 57.6 |
| sls2c.pk018.k22 | 4 | 76.4 |
| wlm96.pk0014.a10 | 6 | 54.5 |

Sequence alignments and percent similarity calculations were performed using the Megalign program of the LASARGENE bioinformatics computing suite (DNASTAR Inc., Madison, Wis.). Multiple alignment of the sequences and percent similarity calculations were performed using the Clustal method of alignment (Higgins, D. G. and Sharp, P.

M. (1989) *CABIOS.* 5:151–153) using the default parameters (GAP PENALTY=10, GAP LENGTH PENALTY=10).

Sequence alignments and BLAST scores and probabilities indicate that the instant nucleic acid fragments encode entire wheat and substantial portions of corn and soybean anti-silencing protein 1. These sequences represent the first plant sequences encoding anti-silencing protein 1.

Example 4

Characterization of cDNA Clones Encoding Polycomb Group Proteins

The BLASTX search using the nucleotide sequences from clones ccl.pk0026.c11, cen1.pk0089.c7, cen3n.pk0140.c7 and wdr1.pk0002.e12 revealed similarity of the proteins encoded by the cDNAs to Polycomb-group proteins from *Arabidopsis thaliana* (GenBank Accession No. Y10580; NCBI General Identifier No. 1903019). The BLAST results for each of these ESTs are shown in Table 5:

TABLE 5

BLAST Results for Clones Encoding Polypeptides Homologous to Polycomb-group Proteins

| Clone | BLAST pLog Score GenBank Accession No. Y10580 |
| --- | --- |
| cc1.pk0026.c11 | 7.88 |
| cen1.pk0089.c7 | 37.72 |
| cen3n.pk0140.c7 | 14.38 |
| wdr1.pk0002.e12 | 23.77 |

The sequence of the entire cDNA insert in clone ccl.pk0026.c11 was determined and is shown in SEQ ID NO:8; the deduced amino acid sequence of this cDNA is shown in SEQ ID NO:9. The amino acid sequence set forth in SEQ ID NO:9 was evaluated by BLASTP, yielding a pLog value of >250 versus the *Arabidopsis thaliana* polycomb group protein sequence (NCBI General Identifier No. 3242729; SEQ ID NO:12). FIGS. 2A, 2B, 2C, and 2D presents an alignment of the amino acid sequence set forth in SEQ ID NO:9 and the *Arabidopsis thaliana* polycomb group protein sequence. The amino acid sequence set forth in SEQ ID NO:9 is 50.9% similar to the *Arabidopsis thaliana* polycomb group protein sequence. The sequence of the entire cDNA insert in clone wdr1.pk0002.e12 was determined and is shown in SEQ ID NO:10; the deduced amino acid sequence of this cDNA is shown in SEQ ID NO:11. The amino acid sequence set forth in SEQ ID NO:11 was evaluated by BLASTP, yielding a pLog value of 136.0 versus the *Arabidopsis thaliana* curly leaf protein (polycomb group) sequence (NCBI General Identifier No. 4185507; SEQ ID NO:13). FIGS. 3A and 3B presents an alignment of the amino acid sequence set forth in SEQ ID NO:11 and the *Arabidopsis thaliana* curly leaf protein (polycomb group) sequence. The amino acid sequence set forth in SEQ ID NO:11 is 61.8% similar to the *Arabidopsis thaliana* polycomb group protein sequence.

Sequence alignments and percent similarity calculations were performed using the Megalign program of the LASAR-GENE bioinformatics computing suite (DNASTAR Inc., Madison, Wis.). Pairwise alignment of the sequences and percent similarity calculations were performed using the Clustal method of alignment (Higgins, D. G. and Sharp, P. M. (1989) *CABIOS.* 5:151–153) using the default parameters (KTUPLE=1, GAP PENALTY=3, WINDOW=5, DIAGONALS SAVED=5).

Sequence alignments and BLAST scores and probabilities indicate that the instant nucleic acid fragments encode entire corn and a substantial portion of wheat polycomb group proteins. These sequences represent the first monocot sequences encoding polycomb group proteins.

Example 5

Expression of Chimeric Genes in Monocot Cells

A chimeric gene comprising a cDNA encoding transcription and gene expression regulators in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (Nco I or Sma I) can be incorporated into the oligonucleotides to provide proper orientation of the DNA fragment when inserted into the digested vector pML103 as described below. Amplification is then performed in a standard PCR. The amplified DNA is then digested with restriction enzymes Nco I and SmaI and fractionated on an agarose gel. The appropriate band can be isolated from the gel and combined with a 4.9 kb Nco I-Sma I fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb Sal I-Nco I promoter fragment of the maize 27 kD zein gene and a 0.96 kb Sma I-Sal I fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding a transcription or gene expression regulator, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al., (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) Nature 313:810–812) and the 3' region of the nopaline synthase gene from the T-DNA of the Ti plasmid of Agrobacterium tumefaciens.

The particle bombardment method (Klein T M et al., (1987) Nature 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al., (1990) Bio/Technology 8:833–839).

Example 6

Expression of Chimeric Genes in Dicot Cells

A seed-specific expression cassette composed of the promoter and transcription terminator from the gene encoding the β subunit of the seed storage protein phaseolin from the bean Phaseolus vulgaris (Doyle et al. (1986) J. Biol. Chem. 261:9228–9238) can be used for expression of the instant transcription or gene expression regulator in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding a transcription or gene expression regulator. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein T. M. et al. (1987) Nature (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) Nature 313:810–812), the hygromycin phosphotransferase gene from plasmid pJR225 (from E. coli; Gritz et al. (1983) Gene 25:179–188) and the 3' region of the nopaline synthase gene from the T-DNA of the Ti plasmid of Agrobacterium tumefaciens. The seed expression cassette comprising the phaseolin 5' region, the fragment encoding the transcription or gene expression regulator and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Chimeric Genes in Microbial Cells

The cDNAs encoding the instant transcription or gene expression regulator can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the transcription or gene expression regulator are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methyl-sulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

What is claimed is:

1. An isolated polynucleotide comprising:
   (a) a nucleotide sequence encoding a polypeptide having polycomb-group protein activity, wherein the amino acid sequence of the polypeptide and the amino acid sequence of SEQ ID NO:9 have at least 80% identity, or
   (b) the complement of the nucleotide sequence, wherein said polycomb-group protein activity comprises maintenance of heterochromatin structure.

2. The polynucleotide of claim 1, wherein the amino acid sequence of the polypeptide and the amino acid sequence of SEQ ID NO:9 have at least 90% identity.

3. The polynucleotide of claim 1, wherein the amino acid sequence of the polypeptide and the amino acid sequence of SEQ ID NO:9 have at least 95% identity.

4. The polynucleotide of claim 1, wherein the nucleotide sequence comprises the nucleotide sequence of SEQ ID NO:8.

5. The polynucleotide of claim 1, wherein the amino acid sequence of the polypeptide comprises the amino acid sequence of SEQ ID NO:9.

6. A vector comprising the polynucleotide of claim 1.

7. A chimeric gene comprising the polynucleotide of claim 1, operably linked to a regulatory sequence.

8. A method for transforming a cell comprising transforming a cell with the polynucleotide of claim 1.

9. A cell comprising the chimeric gene of claim 7.

10. A method for producing a plant comprising transforming a plant cell with the polynucleotide of claim 1 and regenerating a plant from the transformed plant cell.

11. A plant comprising the chimeric gene of claim 7.

12. A seed comprising the chimeric gene of claim 7.

13. A method for isolating a polypeptide encoded by the polynucleotide of claim 1 comprising isolating the polypeptide from a cell containing a chimeric gene comprising the polynucleotide operably linked to a regulatory sequence.

* * * * *

UNITED STATES PATENT AND TRADEMARK OFFICE
CERTIFICATE OF CORRECTION

PATENT NO.      : 6,559,354 B1
DATED           : May 6, 2003
INVENTOR(S)     : Odell Joan T. and Rafalski J. Antoni It is certified that error appears in the above-identified patent and that said Letters Patent is hereby corrected as shown below:

<u>Title page,</u>
Item [75], Inventors, please delete "Hongchang Ma, Omolayo O, Famodu nee Morakinyo, and Emil M. Orozco, Jr."

Signed and Sealed this

Eighth Day of June, 2004

JON W. DUDAS
*Acting Director of the United States Patent and Trademark Office*

SEQUENCE LISTING

<160> NUMBER OF SEQ ID NOS: 13

<210> SEQ ID NO 1
<211> LENGTH: 1018
<212> TYPE: DNA
<213> ORGANISM: Zea mays

<400> SEQUENCE: 1

```
gcacgagagc ttctctggcc ctctcactcc aaacatcggg ctccaggccg tctcccgcca      60
acccaaattc gcttcccgcc gctccccatt aaacccgctt gaaaggtcgc gccctcgagc     120
agagcaaccc ctgaccacaa atccgatccg cagccgccgt gcctcgcttt cgtcttttcc     180
cctctgctcg agtacgagcg gctactcccg gcggctgcgg cggcggcgat gagcgcggtg     240
aacatcacca acgtggcggt gctggataac cccaccgcct tcctcaatcc cttccaattt     300
gagatctcct acgagtgcct cgtgcccctc gacgacgatc tggagtggaa gcttatatat     360
gttggatcag ctgaagatga aaactacgat caacagcttg agagcgtgct tgttggccct     420
gtcaatgttg ggacctaccg ttttgtcctt caggctgacc caccggatcc ctcaaagata     480
```

-continued

```
cgtgaggaag acataattgg tgtgactgtg ctgctattga catgctctta catgggccag      540
gagttcatga gagtaggcta ctacgtgaac aatgattatg atgatgaaca attgagagaa      600
gagcctccag caaaggtgct aattgacagg gtgcaaagaa atatcttggc cgacaagccc      660
cgagtcacca agttccctat caacttccat cctgaaccca gtacaggccc ggggcagcag      720
cagcaggaac cccagacgac ctcgccagaa accacacag gcaatggcga ggccaatggt       780
agcaagcctg aggctgacca atgaacacag ttggcttcag atattttgat gcgtgcccct      840
tacaggttgt gctgtaatat tacaaacggg attagtggtt gtgcattgcc ctgggatcct      900
gaactctgtt ctgtaacttg agatgcaaat gctgggtacc tggatgtttt cttaagcacg      960
agtatttcag cctaaaaaaa aaaaaaaaaa aaaaaaaaaa aaaaaaaaaa aaaaaaa        1018
```

<210> SEQ ID NO 2
<211> LENGTH: 151
<212> TYPE: PRT
<213> ORGANISM: Zea mays
<400> SEQUENCE: 2

```
Met Ser Ala Val Asn Ile Thr Asn Val Ala Val Leu Asp Asn Pro Thr
 1               5                  10                  15

Ala Phe Leu Asn Pro Phe Gln Phe Glu Ile Ser Tyr Glu Cys Leu Val
                20                  25                  30

Pro Leu Asp Asp Asp Leu Glu Trp Lys Leu Ile Tyr Val Gly Ser Ala
            35                  40                  45

Glu Asp Glu Asn Tyr Asp Gln Gln Leu Glu Ser Val Leu Val Gly Pro
         50                  55                  60

Val Asn Val Gly Thr Tyr Arg Phe Val Leu Gln Ala Asp Pro Pro Asp
 65                  70                  75                  80

Pro Ser Lys Ile Arg Glu Glu Asp Ile Ile Gly Val Thr Val Leu Leu
                 85                  90                  95

Leu Thr Cys Ser Tyr Met Gly Gln Glu Phe Met Arg Val Gly Tyr Tyr
            100                 105                 110

Val Asn Asn Asp Tyr Asp Asp Glu Gln Leu Arg Glu Glu Pro Pro Ala
        115                 120                 125

Lys Val Leu Ile Asp Arg Val Gln Arg Asn Ile Leu Ala Asp Lys Pro
    130                 135                 140

Arg Val Thr Lys Phe Pro Ile
145                 150
```

<210> SEQ ID NO 3
<211> LENGTH: 460
<212> TYPE: DNA
<213> ORGANISM: Glycine max
<400> SEQUENCE: 3

```
gactgcactg catgttttga atctgaattt ggaaatcctt taaaccttta tagagactaa       60
tcaacctctc tctttcaaca tgtctgtcgt ctcacttctc ggtgttactg ttcgcaacaa      120
tccagctaaa tttgtagatc cttatgagtt tgaaatcacc ttcgagtgtc tcgaggcatt      180
acaaaaggat cttgaatgga aattgaccta tgttggttcg ccacatctg atgagcatga       240 tcaagaactc gattctctcc tcgttggtcc cattcccgtc ggcgtaaaca aatttctctt      300
ccaggcagat gcgcccgata ccaagcgaat cccagatgca agaaattctc ggtgttactg      360
tcattcttct cacttgcgcc tatgatggta aagagtttgt tcgagttggc tattatgtca      420
acaacgagta tgattctgag gaattgaacg ccgattcacc                            460
```

<210> SEQ ID NO 4
<211> LENGTH: 85
<212> TYPE: PRT
<213> ORGANISM: Glycine max

<400> SEQUENCE: 4

```
Met Ser Val Val Ser Leu Leu Gly Val Thr Val Arg Asn Asn Pro Ala
  1               5                  10                  15

Lys Phe Val Asp Pro Tyr Glu Phe Glu Ile Thr Phe Glu Cys Leu Glu
             20                  25                  30

Ala Leu Gln Lys Asp Leu Glu Trp Lys Leu Thr Tyr Val Gly Ser Ala
         35                  40                  45

Thr Ser Asp Glu His Asp Gln Glu Leu Asp Ser Leu Leu Val Gly Pro
     50                  55                  60

Ile Pro Val Gly Val Asn Lys Phe Leu Phe Gln Ala Asp Ala Pro Asp
 65                  70                  75                  80

Thr Lys Arg Ile Pro
                 85
```

<210> SEQ ID NO 5
<211> LENGTH: 999
<212> TYPE: DNA
<213> ORGANISM: Triticum aestivum

<400> SEQUENCE: 5

```
ctcgtgccga attcggcacg agatctagag aaactatagt tcactttaaa aagccattag     60
agctaattta cattgtgtaa gagaagctac ggcggaagaa aacatgtcgg tagtttcact    120
gctaggcgtc aatgttcttc agaatccggc ccggtttggt gacccatatg agtttgaaat    180
cacgttcgaa tgtttagaaa cactccagaa agatctcgaa tggaagttga cttatgttgg    240
atcagctaca tccaatgatc acgatcaaga gcttgatagc ttactcgttg ggcctattcc    300
agttggcgtt aacaaattta ttttcgtagc agaccctccg gacaccaata agataccaga    360
cgccgaaatt ctaggtgtca ccgtcatact tctaacatgt gcttacgacg gtcgagaatt    420
tttccgtgtt ggatactacg tcaataacga gtatgactca gatgaactga acacagaccc    480
tcccgcaaag cccatattag agaaagttcg gcgtaatatt ctggccgaga agccaagggt    540
aactcgcttt gcaataaagt gggactctga tgattctgcg ccaccactct atccacctga    600
gcaaccagaa gcagacttag tggccgatgg tgaagaatac ggtgccgaag aggctgagga    660
cgaagacgaa gaagagtctc ggatgggcc agaagttcca gcagaccctg acgtcatgat    720
cgatgattct gaagccgcag gtgccatggt agagactgtc aaagcaaccg aagaagaatc    780
cgatgccggc agcgaagatt tggaagctga agcagtggga agcgaggaag atgagattga    840
agaagatgaa gagcgcgagg atgaacctga agaagccatg gatttggatg gcgcaggtaa    900
acgaaacgct gctatatcta gcagcaacaa caccgatacc acaatggctc attaatttaa    960
ttttgaaaat tcgaaaaaaa aaaaaaaaaa aaaaaaaa                            999
```

<210> SEQ ID NO 6
<211> LENGTH: 242
<212> TYPE: PRT
<213> ORGANISM: Triticum aestivum

<400> SEQUENCE: 6

```
Met Ser Val Val Ser Leu Leu Gly Val Asn Val Leu Gln Asn Pro Ala
  1               5                  10                  15
```

```
Arg Phe Gly Asp Pro Tyr Glu Phe Glu Ile Thr Phe Glu Cys Leu Glu
            20                  25                  30

Thr Leu Gln Lys Asp Leu Glu Trp Lys Leu Thr Tyr Val Gly Ser Ala
        35                  40                  45

Thr Ser Asn Asp His Asp Gln Glu Leu Asp Ser Leu Leu Val Gly Pro
    50                  55                  60

Ile Pro Val Gly Val Asn Lys Phe Ile Phe Val Ala Asp Pro Pro Asp
65                  70                  75                  80

Thr Asn Lys Ile Pro Asp Ala Glu Ile Leu Gly Val Thr Val Ile Leu
                85                  90                  95

Leu Thr Cys Ala Tyr Asp Gly Arg Glu Phe Phe Arg Val Gly Tyr Tyr
            100                 105                 110

Val Asn Asn Glu Tyr Asp Ser Asp Glu Leu Asn Thr Asp Pro Pro Ala
        115                 120                 125

Lys Pro Ile Leu Glu Lys Val Arg Arg Asn Ile Leu Ala Glu Lys Pro
    130                 135                 140

Arg Val Thr Arg Phe Ala Ile Lys Trp Asp Ser Asp Ser Ala Pro
145                 150                 155                 160

Pro Leu Tyr Pro Pro Glu Gln Pro Glu Ala Asp Leu Val Ala Asp Gly
                165                 170                 175

Glu Glu Tyr Gly Ala Glu Ala Glu Asp Glu Asp Glu Glu Ser
            180                 185                 190

Ala Asp Gly Pro Glu Val Pro Ala Asp Pro Val Met Ile Asp Asp
        195                 200                 205

Ser Glu Ala Ala Gly Ala Met Val Glu Thr Val Lys Ala Thr Glu Glu
    210                 215                 220

Glu Ser Asp Ala Gly Ser Glu Asp Leu Glu Ala Glu Ser Ser Gly Ser
225                 230                 235                 240

Glu Glu

<210> SEQ ID NO 7
<211> LENGTH: 279
<212> TYPE: PRT
<213> ORGANISM: Saccharomyces cerevisiae

<400> SEQUENCE: 7

Met Ser Ile Val Ser Leu Leu Gly Ile Lys Val Leu Asn Asn Pro Ala
1               5                   10                  15

Lys Phe Thr Asp Pro Tyr Glu Phe Glu Ile Thr Phe Glu Cys Leu Glu
            20                  25                  30

Ser Leu Lys His Asp Leu Glu Trp Lys Leu Thr Tyr Val Gly Ser Ser
        35                  40                  45

Arg Ser Leu Asp His Asp Gln Glu Leu Asp Ser Ile Leu Val Gly Pro
    50                  55                  60

Val Pro Val Gly Val Asn Lys Phe Val Phe Ser Ala Asp Pro Pro Ser
65                  70                  75                  80

Ala Glu Leu Ile Pro Ala Ser Glu Leu Val Ser Val Thr Val Ile Leu
                85                  90                  95

Leu Ser Cys Ser Tyr Asp Gly Arg Glu Phe Val Arg Val Gly Tyr Tyr
            100                 105                 110

Val Asn Asn Glu Tyr Asp Glu Glu Leu Arg Glu Asn Pro Pro Ala
        115                 120                 125

Lys Val Gln Val Asp His Ile Val Arg Asn Ile Leu Ala Glu Lys Pro
    130                 135                 140
```

```
Arg Val Thr Arg Phe Asn Ile Val Trp Asp Asn Glu Asn Glu Gly Asp
145                 150                 155                 160

Leu Tyr Pro Pro Glu Gln Pro Gly Val Asp Glu Glu Glu Glu Asp
            165                 170                 175

Asp Glu Glu Glu Asp Asp Asp Glu Asp Asp Glu Asp Asp Glu Asp Asp
            180                 185                 190

Asp Gln Glu Asp Gly Glu Gly Glu Ala Glu Glu Ala Ala Glu Glu Glu
            195                 200                 205

Glu Glu Glu Glu Glu Lys Thr Glu Asp Asn Glu Thr Asn Leu Glu Glu
            210                 215                 220

Glu Glu Glu Asp Ile Glu Asn Ser Asp Gly Asp Glu Glu Gly Glu
225                 230                 235                 240

Glu Glu Val Gly Ser Val Asp Lys Asn Glu Asp Gly Asn Asp Lys Lys
                245                 250                 255

Arg Arg Lys Ile Glu Gly Gly Ser Thr Asp Ile Glu Ser Thr Pro Lys
            260                 265                 270

Asp Ala Ala Arg Ser Thr Asn
            275

<210> SEQ ID NO 8
<211> LENGTH: 3148
<212> TYPE: DNA
<213> ORGANISM: Zea mays

<400> SEQUENCE: 8
gcacgagggg tgatggaagc agaggctgcc gcggcggtag tggcgtcgtc cgcatctgcc      60
tcggcttccg cgggccggtc tcgcccatct agcagcgccg cccaggtcac cagtaattcg     120
gctgtgcgag ctggagaaga aaatgctgcc tccctctatg ttttatctgt tattgactcg     180
ttaaaaaaga ggattaccgc agatcgtttg acttacatta agaataggat aggggagaac     240
aagactaata tcagcagcta tacacagagg acttacaatt tatcaaaaaa taggcaaatt     300 agtcatcaa aggtactga ttcagcatca aatttgctca caaaaaggca agatgatgcg      360
ctatgcaccc tgcatagtct tgatattatt ccggttgaca agatggtgg tactttttcaa    420 gacgaaagtc ctttctcttc atctaatgtt atgtttggtg gaaatcttgg tcccaagaat    480
gctattatta gaccaattaa actaccagaa gtgccaaagc ttccacctta tacaacatgg    540 atattttttgg acaggaacca aaggatgaca gaagaccaat ctgtacttgg tcgacggagg   600
atttactatg ataccagttg tggtgaagct ctaatttgca gtgatagtga agatgaagcc   660
attgaagatg aggaggaaaa aaaggaattt aaacattctg aagatcacat tattcggatg   720
acagttcaag aatgtggcat gtctgatgct gtactgcaaa cgctagctcg acacatggag   780
cgggctgctg atgacataaa ggccaggtat gaaattctgc atggtgagaa aactaaggat   840
tcttgcaaga aagggactga gcataatgtc aaagtggaag atttgtactg tgacaaagat   900
ttggatgcag cattggattc ttttgacaat ctcttctgtc gaccacgaga caacgatgt    960 ctagtgtttg attgcaagct acatgggtgt tctcaagatt tagtatttcc tacagaaaaa  1020
caaccagctt ggagtggcgt tgatgacagt gtaccctgtg gtattcattg ccataaactg   1080
gcatctgaac cagatgctgc tgctggtgct gatcacatgc tttttgatgt tgaggagcca  1140
actcactcat cagacaatgt gatgaaccag ccaggttcaa ataggaaaaa gaacggctcc  1200
agtggaagga agactaaatc tcaacaaagt gaaagctctt caactgcaag agttatctca   1260
gaaagcagtg attcggaagt acatccaata agcaataaat ctccacaaca ctcccctagt   1320
```

-continued

```
ccctcaaaag ttaaaattgg gccgaaaggt ggaatcagaa agattaccaa tagacgaatc    1380
gctgagagaa ttcttatgag tgtgaagaaa ggacaaaggg aaatggcatc atctgattct    1440
aattttgtta gtggatatct tttggcaagg gacatgaagc ttaggtctga tacacgaaat    1500
ggaaataagg aattaattgt atcctcacaa cagagttctc caagcacaag aagttccaaa    1560
aagaagagta cacctcaaat tgggaacagc tcagcttttg ctgaggctca taatgattca    1620
acagaggaag caaataaccg tcattcagca acagatggtt acgatagttc aaggaaagaa    1680
gaattcgtca atgagaattt atgcaagcag gaggtgtact tgagatcatg gaaggcaatt    1740
gagcagggac ttcttgtgaa aggattagag attttttggaa ggaacagttg tttaattgct    1800
cggaaccttc ttggtggaat gaagacgtgc aaagatgttt ttcaatatat gaattatatt    1860
gaaaacaaca gtgcctctgg agctcttagt ggtgttgatt ctcttgttaa aggatatatt    1920
aagggtactg agttgcgcac aagatcaaga tattttagaa ggcgaggtaa agtccgtcgt    1980
ttgaagtaca cctggaaatc tgcaggttac aatttcaaaa ggattaccga aggaaggat    2040 cagccttgtc gacaatataa tccttgtggt tgtcaatcta catgcggaaa gcagtgtcca    2100
tgtctttcaa atgggacatg ttgtgagaaa tactgtgggt gtccaaaaat ttgcaagaat    2160
cgttttcgag gatgtcactg tgcaagagc cagtgtcgca gccgccaatg tccatgtttt    2220
gcagctgaca gggaatgcga tccggatgtt tgcagaaact gttgggttgg gtgtggtgat    2280
ggtacattgg gagttccaaa ccagagagga gataattatg aatgccggaa catgaaactg    2340
cttcttaaac aacaacaaag ggtcttactt ggaagatcag atgtctctgg ctggggagca    2400
ttcctcaaga atagtgttag caaacatgaa taccttggtg agtacactgg ggaactaatc    2460
tcacacaaag aagcagataa gcgtggaaag atatatgatc gtgagaactc atcgttcctt    2520
ttcaacctga caatgagta tgttcttgac gcatacagaa tgggtgacaa gctgaaattt    2580
gccaaccatg cccctgaccc gaattgctat gccaaggtta tcatggtaac tggtgatcat    2640
agagtgggca tattcgccaa agaaagaatc ctcgctggtg aagagttatt ctacgattac    2700
cgctatgagc ctgacagagc tcctgcttgg gcccgtaagc ctgaggcgtc gggagcaaag    2760
gatgatgggc aaccgttcaa tgggcgtgca agaagctcg cccaaaacaa ccgaggctga    2820
atctgatttg attctttcat tgttaggaca aatttggcag ccattcaact aatacaagga    2880
acctgtcatt cataggcccc aatttatttg aactcgtcac ttgtaactcg tatgtgcttg    2940
aattctccat ggcatctggt cctgccatcc gtagagttag gtcccgtttg ttttgtttgt    3000
tttgaggaac taaaaattaa tccctctatt ttagtcacat tgagtctcta gattgtcaaa    3060
cggcgggact aaaacaaaga ctaaactatt tgtctctagt tcctcaagcc atgacttaaa    3120
gggaataaat cacataaatt ttatttta                                      3148
```

<210> SEQ ID NO 9
<211> LENGTH: 921
<212> TYPE: PRT
<213> ORGANISM: Zea mays

<400> SEQUENCE: 9

```
Val Ala Ser Ser Ala Ser Ala Ser Ala Gly Arg Ser Arg Pro
  1               5                  10                  15

Ser Ser Ser Ala Ala Gln Val Thr Ser Asn Ser Ala Val Arg Ala Gly
             20                  25                  30

Glu Glu Asn Ala Ala Ser Leu Tyr Val Leu Ser Val Ile Asp Ser Leu
         35                  40                  45
```

-continued

```
Lys Lys Arg Ile Thr Ala Asp Arg Leu Thr Tyr Ile Lys Asn Arg Ile
     50                  55                  60

Gly Glu Asn Lys Thr Asn Ile Ser Ser Tyr Thr Gln Arg Thr Tyr Asn
 65                  70                  75                  80

Leu Ser Lys Asn Arg Gln Ile Ser Thr Ser Lys Gly Thr Asp Ser Ala
                 85                  90                  95

Ser Asn Leu Leu Thr Lys Arg Gln Asp Asp Ala Leu Cys Thr Leu His
            100                 105                 110

Ser Leu Asp Ile Ile Pro Val Asp Lys Asp Gly Gly Thr Phe Gln Asp
        115                 120                 125

Glu Ser Pro Phe Ser Ser Asn Val Met Phe Gly Gly Asn Leu Gly
    130                 135                 140

Pro Lys Asn Ala Ile Ile Arg Pro Ile Lys Leu Pro Glu Val Pro Lys
145                 150                 155                 160

Leu Pro Pro Tyr Thr Thr Trp Ile Phe Leu Asp Arg Asn Gln Arg Met
                165                 170                 175

Thr Glu Asp Gln Ser Val Leu Gly Arg Arg Ile Tyr Tyr Asp Thr
                180                 185                 190

Ser Cys Gly Glu Ala Leu Ile Cys Ser Asp Ser Glu Asp Glu Ala Ile
        195                 200                 205

Glu Asp Glu Glu Glu Lys Lys Glu Phe Lys His Ser Glu Asp His Ile
    210                 215                 220

Ile Arg Met Thr Val Gln Glu Cys Gly Met Ser Asp Ala Val Leu Gln
225                 230                 235                 240

Thr Leu Ala Arg His Met Glu Arg Ala Ala Asp Asp Ile Lys Ala Arg
                245                 250                 255

Tyr Glu Ile Leu His Gly Glu Lys Thr Lys Asp Ser Cys Lys Lys Gly
                260                 265                 270

Thr Glu His Asn Val Lys Val Glu Asp Leu Tyr Cys Asp Lys Asp Leu
            275                 280                 285

Asp Ala Ala Leu Asp Ser Phe Asp Asn Leu Phe Cys Arg Pro Arg Glu
    290                 295                 300

Gln Arg Cys Leu Val Phe Asp Cys Lys Leu His Gly Cys Ser Gln Asp
305                 310                 315                 320

Leu Val Phe Pro Thr Glu Lys Gln Pro Ala Trp Ser Gly Val Asp Asp
                325                 330                 335

Ser Val Pro Cys Gly Ile His Cys His Lys Leu Ala Ser Glu Pro Asp
                340                 345                 350

Ala Ala Ala Gly Ala Asp His Met Leu Phe Asp Val Glu Glu Pro Thr
        355                 360                 365

His Ser Ser Asp Asn Val Met Asn Gln Pro Gly Ser Asn Arg Lys Lys
    370                 375                 380

Asn Gly Ser Ser Gly Arg Lys Thr Lys Ser Gln Gln Ser Glu Ser Ser
385                 390                 395                 400

Ser Thr Ala Arg Val Ile Ser Glu Ser Ser Asp Ser Glu Val His Pro
                405                 410                 415

Ile Ser Asn Lys Ser Pro Gln His Ser Pro Ser Pro Ser Lys Val Lys
                420                 425                 430

Ile Gly Pro Lys Gly Gly Ile Arg Lys Ile Thr Asn Arg Arg Ile Ala
            435                 440                 445

Glu Arg Ile Leu Met Ser Val Lys Lys Gly Gln Arg Glu Met Ala Ser
    450                 455                 460
```

-continued

```
Ser Asp Ser Asn Phe Val Ser Gly Tyr Leu Leu Ala Arg Asp Met Lys
465                 470                 475                 480

Leu Arg Ser Asp Thr Arg Asn Gly Asn Lys Glu Leu Ile Val Ser Ser
                485                 490                 495

Gln Gln Ser Ser Pro Ser Thr Arg Ser Ser Lys Lys Ser Thr Pro
            500                 505                 510

Gln Ile Gly Asn Ser Ser Ala Phe Ala Glu Ala His Asn Asp Ser Thr
            515                 520                 525

Glu Glu Ala Asn Arg His Ser Ala Thr Asp Gly Tyr Asp Ser Ser
        530                 535                 540

Arg Lys Glu Glu Phe Val Asn Glu Asn Leu Cys Lys Gln Glu Val Tyr
545                 550                 555                 560

Leu Arg Ser Trp Lys Ala Ile Glu Gln Gly Leu Leu Val Lys Gly Leu
                565                 570                 575

Glu Ile Phe Gly Arg Asn Ser Cys Leu Ile Ala Arg Asn Leu Leu Gly
                580                 585                 590

Gly Met Lys Thr Cys Lys Asp Val Phe Gln Tyr Met Asn Tyr Ile Glu
                595                 600                 605

Asn Asn Ser Ala Ser Gly Ala Leu Ser Gly Val Asp Ser Leu Val Lys
            610                 615                 620

Gly Tyr Ile Lys Gly Thr Glu Leu Arg Thr Arg Ser Arg Tyr Phe Arg
625                 630                 635                 640

Arg Arg Gly Lys Val Arg Arg Leu Lys Tyr Thr Trp Lys Ser Ala Gly
                645                 650                 655

Tyr Asn Phe Lys Arg Ile Thr Glu Arg Lys Asp Gln Pro Cys Arg Gln
                660                 665                 670

Tyr Asn Pro Cys Gly Cys Gln Ser Thr Cys Gly Lys Gln Cys Pro Cys
            675                 680                 685

Leu Ser Asn Gly Thr Cys Cys Glu Lys Tyr Cys Gly Cys Pro Lys Ile
        690                 695                 700

Cys Lys Asn Arg Phe Arg Gly Cys His Cys Ala Lys Ser Gln Cys Arg
705                 710                 715                 720

Ser Arg Gln Cys Pro Cys Phe Ala Ala Asp Arg Glu Cys Asp Pro Asp
                725                 730                 735

Val Cys Arg Asn Cys Trp Val Gly Cys Gly Asp Gly Thr Leu Gly Val
                740                 745                 750

Pro Asn Gln Arg Gly Asp Asn Tyr Glu Cys Arg Asn Met Lys Leu Leu
        755                 760                 765

Leu Lys Gln Gln Gln Arg Val Leu Leu Gly Arg Ser Asp Val Ser Gly
        770                 775                 780

Trp Gly Ala Phe Leu Lys Asn Ser Val Ser Lys His Glu Tyr Leu Gly
785                 790                 795                 800

Glu Tyr Thr Gly Glu Leu Ile Ser His Lys Glu Ala Asp Lys Arg Gly
                805                 810                 815

Lys Ile Tyr Asp Arg Glu Asn Ser Ser Phe Leu Phe Asn Leu Asn Asn
                820                 825                 830

Glu Tyr Val Leu Asp Ala Tyr Arg Met Gly Asp Lys Leu Lys Phe Ala
            835                 840                 845

Asn His Ala Pro Asp Pro Asn Cys Tyr Ala Lys Val Ile Met Val Thr
        850                 855                 860

Gly Asp His Arg Val Gly Ile Phe Ala Lys Glu Arg Ile Leu Ala Gly
865                 870                 875                 880
```

Glu Glu Leu Phe Tyr Asp Tyr Arg Tyr Glu Pro Asp Arg Ala Pro Ala
                885                 890                 895

Trp Ala Arg Lys Pro Glu Ala Ser Gly Ala Lys Asp Asp Gly Gln Pro
    900                 905                 910

Phe Asn Gly Arg Ala Lys Lys Leu Ala
    915                 920

<210> SEQ ID NO 10
<211> LENGTH: 1406
<212> TYPE: DNA
<213> ORGANISM: Triticum aestivum
<220> FEATURE:
<221> NAME/KEY: unsure
<222> LOCATION: (513)
<223> OTHER INFORMATION: n=a, c, g, or t

<400> SEQUENCE: 10

| | | | | | |
|---|---|---|---|---|---|
| ctttctcatt | ggagtaccct | agagagggat | ttatatctga | agggaataga | gatatttggg | 60 |
| aaaaatagct | gtctaatagt | cagaaaccta | ttatgtggcc | tgaaaacctg | catggaagtg | 120 |
| gctagctaca | tgtacaacaa | tggtgcagca | acatgagta | aatccatttc | gggcgatttc | 180 |
| acagaaactg | aacaaaacta | catggagcaa | ggcatggttg | tgagaacaaa | agtctgtcgt | 240 |
| cgaaggggca | gaactcgaaa | gcacaaatat | ccttcgaagg | ctgcagggca | tccagccatt | 300 |
| aggaaaaaag | ttggtgatgg | gaagcaatgt | gacagacagt | atacaccatg | tgggtgccag | 360 |
| gaaatgtgca | acaaaaattg | ccctgtgtg | gaaatggga | catgctgtga | gaaatactgt | 420 |
| gggtgttcaa | aaagctgcaa | aaacagattt | agaggctgtc | attgtgcaaa | aatcagtgca | 480 |
| gaagcaggca | atgcccatgt | tttgctgcca | tcngggaatg | tgatccggat | gttttgcaga | 540 |
| aactgctggg | gtgagctgtg | gagtggttca | cctaggcgag | ccaccaagaa | agaggtgatg | 600 |
| gttacccart | gcggaaacat | gaagctcctc | ctaaaacaac | aacaaaggat | tttgcttgga | 660 |
| aaatcggacg | ttgcaggatg | gggtgcgttc | attaagaacc | ctgtgcataa | gaatgactat | 720 |
| cttggagagt | acactggtga | attgatttct | cacaagaag | cagacaaacg | cggcaaaatt | 780 |
| tatgaccggg | caaactcttc | gttcctcttt | gatttaaatg | accagtttgt | attggatgca | 840 |
| tatcggaagg | gggataaatt | gaagttcgca | aatcactcct | ccagccccaa | ctgctatgca | 900 |
| aaggtgatga | tggtggccgg | tgaccatcgg | gttggtatct | atgcaaggga | gcatattgaa | 960 |
| gctagtgccg | aactcttcta | tgattaccgg | tatggaccgg | accaagcccc | agcctgggct | 1020 |
| aggagaccag | aaggagcaaa | gaaggatgaa | gcgtctggtt | ctcatcgtcg | agcacacaaa | 1080 |
| gttgcttgat | agctgaagag | cagctccgat | gatagaagct | gctgtaaact | attgccatac | 1140 |
| aacaaacttc | tatcccagtt | cattatacaa | ggcagaccga | ttgttggcct | gataaaaaga | 1200 |
| atgtgtattc | cttaagaaat | aaagtcccaa | gtaccaacct | tgtggatgac | tgacaaataa | 1260 |
| gcttttattg | atagtctgaa | tgataacata | attgtgtgtg | aacatgcttg | cttgtactct | 1320 |
| tgagaacttg | tacatggttt | tcaaactgga | gttgcctgaa | catctacatg | ttgaagtgga | 1380 |
| ccaagatggc | aataaaaatt | tatgct | | | | 1406 |

<210> SEQ ID NO 11
<211> LENGTH: 359
<212> TYPE: PRT
<213> ORGANISM: Triticum aestivum

<400> SEQUENCE: 11

Ser His Trp Ser Thr Leu Glu Arg Asp Leu Tyr Leu Lys Gly Ile Glu
 1               5                  10                  15

```
Ile Phe Gly Lys Asn Ser Cys Leu Ile Val Arg Asn Leu Leu Cys Gly
             20                  25                  30

Leu Lys Thr Cys Met Glu Val Ala Ser Tyr Met Tyr Asn Asn Gly Ala
         35                  40                  45

Ala Asn Met Ser Lys Ser Ile Ser Gly Asp Phe Thr Glu Thr Glu Gln
     50                  55                  60

Asn Tyr Met Glu Gln Gly Met Val Val Arg Thr Lys Val Cys Arg Arg
 65                  70                  75                  80

Arg Gly Arg Thr Arg Lys His Lys Tyr Pro Ser Lys Ala Ala Gly His
             85                  90                  95

Pro Ala Ile Arg Lys Lys Val Gly Asp Gly Lys Gln Cys Asp Arg Gln
        100                 105                 110

Tyr Thr Pro Cys Gly Cys Gln Glu Met Cys Asn Lys Asn Cys Pro Cys
        115                 120                 125

Val Glu Asn Gly Thr Cys Cys Glu Lys Tyr Cys Gly Cys Ser Lys Ser
    130                 135                 140

Cys Lys Asn Arg Phe Arg Gly Cys His Cys Ala Lys Ile Ser Ala Glu
145                 150                 155                 160

Ala Gly Asn Ala His Val Leu Leu Pro Ser Gly Asn Val Ile Arg Met
                165                 170                 175

Phe Cys Arg Asn Cys Trp Gly Glu Leu Trp Ser Gly Ser Pro Arg Arg
            180                 185                 190

Ala Thr Lys Lys Glu Val Met Val Thr Gln Cys Gly Asn Met Lys Leu
        195                 200                 205

Leu Leu Lys Gln Gln Gln Arg Ile Leu Leu Gly Lys Ser Asp Val Ala
    210                 215                 220

Gly Trp Gly Ala Phe Ile Lys Asn Pro Val His Lys Asn Asp Tyr Leu
225                 230                 235                 240

Gly Glu Tyr Thr Gly Glu Leu Ile Ser His Lys Glu Ala Asp Lys Arg
                245                 250                 255

Gly Lys Ile Tyr Asp Arg Ala Asn Ser Ser Phe Leu Phe Asp Leu Asn
            260                 265                 270

Asp Gln Phe Val Leu Asp Ala Tyr Arg Lys Gly Asp Lys Leu Lys Phe
        275                 280                 285

Ala Asn His Ser Ser Pro Asn Cys Tyr Ala Lys Val Met Met Val
    290                 295                 300

Ala Gly Asp His Arg Val Gly Ile Tyr Ala Arg Glu His Ile Glu Ala
305                 310                 315                 320

Ser Ala Glu Leu Phe Tyr Asp Tyr Arg Tyr Gly Pro Asp Gln Ala Pro
                325                 330                 335

Ala Trp Ala Arg Arg Pro Glu Gly Ala Lys Lys Asp Glu Ala Ser Gly
            340                 345                 350

Ser His Arg Arg Ala His Lys
        355

<210> SEQ ID NO 12
<211> LENGTH: 902
<212> TYPE: PRT
<213> ORGANISM: Arabidopsis thaliana

<400> SEQUENCE: 12

Met Ala Ser Glu Ala Ser Pro Ser Ser Ala Thr Arg Ser Glu Pro
  1               5                  10                  15

Pro Lys Asp Ser Pro Ala Glu Glu Arg Gly Pro Ala Ser Lys Glu Val
             20                  25                  30
```

-continued

```
Ser Glu Val Ile Glu Ser Leu Lys Lys Lys Leu Ala Ala Asp Arg Cys
        35                  40                  45

Ile Ser Ile Lys Lys Arg Ile Asp Glu Asn Lys Lys Asn Leu Phe Ala
 50                  55                  60

Ile Thr Gln Ser Phe Met Arg Ser Ser Met Glu Arg Gly Gly Ser Cys
 65                  70                  75                  80

Lys Asp Gly Ser Asp Leu Leu Val Lys Arg Gln Arg Asp Ser Pro Gly
                 85                  90                  95

Met Lys Ser Gly Ile Asp Glu Ser Asn Asn Asn Arg Tyr Val Glu Asp
                100                 105                 110

Gly Pro Ala Ser Ser Gly Met Val Gln Gly Ser Ser Val Pro Val Lys
            115                 120                 125

Ile Ser Leu Arg Pro Ile Lys Met Pro Asp Ile Lys Arg Leu Ser Pro
130                 135                 140

Tyr Thr Thr Trp Val Phe Leu Asp Arg Asn Gln Arg Met Thr Glu Asp
145                 150                 155                 160

Gln Ser Val Val Gly Arg Arg Ile Tyr Tyr Asp Gln Thr Gly Gly
                165                 170                 175

Glu Ala Leu Ile Cys Ser Asp Ser Glu Glu Ala Ile Asp Asp Glu
            180                 185                 190

Glu Glu Lys Arg Asp Phe Leu Glu Pro Glu Asp Tyr Ile Ile Arg Met
            195                 200                 205

Thr Leu Glu Gln Leu Gly Leu Ser Asp Ser Val Leu Ala Glu Leu Ala
210                 215                 220

Ser Phe Leu Ser Arg Ser Thr Ser Glu Ile Lys Ala Arg His Gly Val
225                 230                 235                 240

Leu Met Lys Glu Lys Glu Val Ser Glu Ser Gly Asp Asn Gln Ala Glu
                245                 250                 255

Ser Ser Leu Leu Asn Lys Asp Met Glu Gly Ala Leu Asp Ser Phe Asp
            260                 265                 270

Asn Leu Phe Cys Arg Arg Cys Leu Val Phe Asp Cys Arg Leu His Gly
            275                 280                 285

Cys Ser Gln Asp Leu Ile Phe Pro Ala Glu Lys Pro Ala Pro Trp Cys
    290                 295                 300

Pro Pro Val Asp Glu Asn Leu Thr Cys Gly Ala Asn Cys Tyr Lys Thr
305                 310                 315                 320

Leu Leu Lys Ser Gly Arg Phe Pro Gly Tyr Gly Thr Ile Glu Gly Lys
                325                 330                 335

Thr Gly Thr Ser Ser Asp Gly Ala Gly Thr Lys Thr Thr Pro Thr Lys
            340                 345                 350

Phe Ser Ser Lys Leu Asn Gly Arg Lys Pro Lys Thr Phe Pro Ser Glu
            355                 360                 365

Ser Ala Ser Ser Asn Glu Lys Cys Ala Leu Glu Thr Ser Asp Ser Glu
    370                 375                 380

Asn Gly Leu Gln Gln Asp Thr Asn Ser Asp Lys Val Ser Ser Ser Pro
385                 390                 395                 400

Lys Val Lys Gly Ser Gly Arg Arg Val Gly Arg Lys Arg Asn Lys Asn
                405                 410                 415

Arg Val Ala Glu Arg Val Pro Arg Lys Thr Gln Lys Arg Gln Lys Lys
            420                 425                 430

Thr Glu Ala Ser Asp Ser Asp Ser Ile Ala Ser Gly Ser Cys Ser Pro
435                 440                 445
```

-continued

```
Ser Asp Ala Lys His Lys Asp Asn Glu Asp Ala Thr Ser Ser Ser Gln
450                 455                 460
Lys His Val Lys Ser Gly Asn Ser Gly Lys Ser Arg Lys Asn Gly Thr
465                 470                 475                 480
Pro Ala Glu Val Ser Asn Asn Ser Val Lys Asp Asp Val Pro Val Cys
                485                 490                 495
Gln Ser Asn Glu Val Ala Ser Glu Leu Asp Ala Pro Gly Ser Asp Glu
            500                 505                 510
Ser Leu Arg Lys Glu Glu Phe Met Gly Glu Thr Val Ser Arg Gly Arg
        515                 520                 525
Leu Ala Thr Asn Lys Leu Trp Arg Pro Leu Glu Lys Ser Leu Phe Asp
    530                 535                 540
Lys Gly Val Glu Ile Phe Gly Met Asn Ser Cys Leu Ile Ala Arg Asn
545                 550                 555                 560
Leu Leu Ser Gly Phe Lys Ser Cys Trp Glu Val Phe Gln Tyr Met Thr
                565                 570                 575
Cys Ser Glu Asn Lys Ala Ser Phe Phe Gly Asp Gly Leu Asn Pro
            580                 585                 590
Asp Gly Ser Ser Lys Phe Asp Ile Asn Gly Asn Met Val Asn Asn Gln
        595                 600                 605
Val Arg Arg Arg Ser Arg Phe Leu Arg Arg Gly Lys Val Arg Arg
    610                 615                 620
Leu Lys Tyr Thr Trp Lys Ser Ala Ala Tyr His Ser Ile Arg Lys Arg
625                 630                 635                 640
Ile Thr Glu Lys Lys Asp Gln Pro Cys Arg Gln Phe Asn Pro Cys Asn
                645                 650                 655
Cys Lys Ile Ala Cys Gly Lys Glu Cys Pro Cys Leu Leu Asn Gly Thr
            660                 665                 670
Cys Cys Glu Lys Tyr Cys Gly Cys Pro Lys Ser Cys Lys Asn Arg Phe
        675                 680                 685
Arg Gly Cys His Cys Ala Lys Ser Gln Cys Arg Ser Arg Gln Cys Pro
    690                 695                 700
Cys Phe Ala Ala Asp Arg Glu Cys Asp Pro Asp Val Cys Arg Asn Cys
705                 710                 715                 720
Trp Val Ile Gly Gly Asp Gly Ser Leu Gly Val Pro Ser Gln Arg Gly
                725                 730                 735
Asp Asn Tyr Glu Cys Arg Asn Met Lys Leu Leu Lys Gln Gln Gln
            740                 745                 750
Arg Val Leu Leu Gly Ile Ser Asp Val Ser Gly Trp Gly Ala Phe Leu
        755                 760                 765
Lys Asn Ser Val Ser Lys His Glu Tyr Leu Gly Glu Tyr Thr Gly Glu
    770                 775                 780
Leu Ile Ser His Lys Glu Ala Asp Lys Arg Gly Lys Ile Tyr Asp Arg
785                 790                 795                 800
Glu Asn Cys Ser Phe Leu Phe Asn Leu Asn Asp Gln Phe Val Leu Asp
                805                 810                 815
Ala Tyr Arg Lys Gly Asp Lys Leu Lys Phe Ala Asn His Ser Pro Glu
            820                 825                 830
Pro Asn Cys Tyr Ala Lys Val Ile Met Val Ala Gly Asp His Arg Val
        835                 840                 845
Gly Ile Phe Ala Lys Glu Arg Ile Leu Ala Gly Glu Glu Leu Phe Tyr
    850                 855                 860
```

-continued

```
Asp Tyr Arg Tyr Glu Pro Asp Arg Ala Pro Ala Trp Ala Lys Lys Pro
865                 870                 875                 880

Glu Ala Pro Gly Ser Lys Lys Asp Glu Asn Val Thr Pro Ser Val Gly
                885                 890                 895

Arg Pro Lys Lys Leu Ala
            900

<210> SEQ ID NO 13
<211> LENGTH: 856
<212> TYPE: PRT
<213> ORGANISM: Arabidopsis thaliana

<400> SEQUENCE: 13

Met Val Thr Asp Asp Ser Asn Ser Ser Gly Arg Ile Lys Ser His Val
  1               5                  10                  15

Asp Asp Asp Asp Gly Glu Glu Glu Asp Arg Leu Glu Gly Leu
                 20                  25                  30

Glu Asn Arg Leu Ser Glu Leu Lys Arg Lys Ile Gln Gly Glu Arg Val
             35                  40                  45

Arg Ser Ile Lys Glu Lys Phe Glu Ala Asn Arg Lys Val Asp Ala
     50                  55                  60

His Val Ser Pro Phe Ser Ala Ala Ser Ser Arg Ala Thr Ala Glu
 65                  70                  75                  80

Asp Asn Gly Asn Ser Asn Met Leu Ser Ser Arg Met Arg Met Pro Leu
                 85                  90                  95

Cys Lys Leu Asn Gly Phe Ser His Gly Val Gly Asp Arg Asp Tyr Val
                100                 105                 110

Pro Thr Lys Asp Val Ile Ser Ala Ser Val Lys Leu Pro Ile Ala Glu
            115                 120                 125

Arg Ile Pro Pro Tyr Thr Thr Trp Ile Phe Leu Asp Arg Asn Gln Arg
    130                 135                 140

Met Ala Glu Asp Gln Ser Val Val Gly Arg Arg Gln Ile Tyr Tyr Glu
145                 150                 155                 160

Gln His Gly Gly Glu Thr Leu Ile Cys Ser Asp Ser Glu Glu Pro
                165                 170                 175

Glu Pro Glu Glu Glu Lys Arg Glu Phe Ser Glu Gly Glu Asp Ser Ile
            180                 185                 190

Ile Trp Leu Ile Gly Gln Glu Tyr Gly Met Gly Glu Glu Val Gln Asp
        195                 200                 205

Ala Leu Cys Gln Leu Leu Ser Val Asp Ala Ser Asp Ile Leu Glu Arg
    210                 215                 220

Tyr Asn Glu Leu Lys Leu Lys Asp Lys Gln Asn Thr Glu Glu Phe Ser
225                 230                 235                 240

Asn Ser Gly Phe Lys Leu Gly Ile Ser Leu Glu Lys Gly Leu Gly Ala
                245                 250                 255

Ala Leu Asp Ser Phe Asp Asn Leu Phe Cys Arg Arg Cys Leu Val Phe
            260                 265                 270

Asp Cys Arg Leu His Gly Cys Ser Gln Pro Leu Ile Ser Ala Ser Glu
    275                 280                 285

Lys Gln Pro Tyr Trp Ser Asp Tyr Glu Gly Asp Arg Lys Pro Cys Ser
290                 295                 300

Lys His Cys Tyr Leu Gln Leu Lys Ala Val Arg Glu Val Pro Glu Thr
305                 310                 315                 320

Cys Ser Asn Phe Ala Ser Lys Ala Glu Glu Lys Ala Ser Glu Glu Glu
                325                 330                 335
```

-continued

```
Cys Ser Lys Ala Val Ser Ser Asp Val Pro His Ala Ala Ser Gly
        340                 345                 350
Val Ser Leu Gln Val Glu Lys Thr Asp Ile Gly Ile Lys Asn Val Asp
            355                 360                 365
Ser Ser Ser Gly Val Glu Gln Glu His Gly Ile Arg Gly Lys Arg Glu
        370                 375                 380
Val Pro Ile Leu Lys Asp Ser Asn Asp Leu Pro Asn Leu Ser Asn Lys
385                 390                 395                 400
Lys Gln Lys Thr Ala Ala Ser Asp Thr Lys Met Ser Phe Val Asn Ser
                405                 410                 415
Val Pro Ser Leu Asp Gln Ala Leu Asp Ser Thr Lys Gly Asp Gln Gly
            420                 425                 430
Gly Thr Thr Asp Asn Lys Val Asn Arg Asp Ser Glu Ala Asp Ala Lys
        435                 440                 445
Glu Val Gly Glu Pro Ile Pro Asp Asn Ser Val His Asp Gly Gly Ser
    450                 455                 460
Ser Ile Cys Gln Pro His His Gly Ser Gly Asn Gly Ala Ile Ile Ile
465                 470                 475                 480
Ala Glu Met Ser Glu Thr Ser Arg Pro Ser Thr Glu Trp Asn Pro Ile
                485                 490                 495
Glu Lys Asp Leu Tyr Leu Lys Gly Val Glu Ile Phe Gly Arg Asn Ser
            500                 505                 510
Cys Leu Ile Ala Arg Asn Leu Leu Ser Gly Leu Lys Thr Cys Leu Asp
        515                 520                 525
Val Ser Asn Tyr Met Arg Glu Asn Glu Val Ser Val Phe Arg Arg Ser
    530                 535                 540
Ser Thr Pro Asn Leu Leu Leu Asp Asp Gly Arg Thr Asp Pro Gly Asn
545                 550                 555                 560
Asp Asn Asp Glu Val Pro Pro Arg Thr Arg Leu Phe Arg Arg Lys Gly
                565                 570                 575
Lys Thr Arg Lys Leu Lys Tyr Ser Thr Lys Ser Ala Gly His Pro Ser
            580                 585                 590
Val Trp Lys Arg Ile Ala Gly Gly Lys Asn Gln Ser Cys Lys Gln Tyr
        595                 600                 605
Thr Pro Cys Gly Cys Leu Ser Met Cys Gly Lys Asp Cys Pro Cys Leu
    610                 615                 620
Thr Asn Glu Thr Cys Cys Glu Lys Tyr Cys Gly Cys Ser Lys Ser Cys
625                 630                 635                 640
Lys Asn Arg Phe Arg Gly Cys His Cys Ala Lys Ser Gln Cys Arg Ser
                645                 650                 655
Arg Gln Cys Pro Cys Phe Ala Ala Gly Arg Glu Cys Asp Pro Asp Val
            660                 665                 670
Cys Arg Asn Cys Trp Val Ser Cys Gly Asp Gly Ser Leu Gly Glu Ala
        675                 680                 685
Pro Arg Arg Gly Glu Gly Gln Cys Gly Asn Met Arg Leu Leu Leu Arg
    690                 695                 700
Gln Gln Gln Arg Ile Leu Leu Gly Lys Ser Asp Val Ala Gly Trp Gly
705                 710                 715                 720
Ala Phe Leu Lys Asn Ser Val Ser Lys Asn Glu Tyr Leu Gly Glu Tyr
                725                 730                 735
Thr Gly Glu Leu Ile Ser His His Glu Ala Asp Lys Arg Gly Lys Ile
            740                 745                 750
```

-continued

```
Tyr Asp Arg Ala Asn Ser Ser Phe Leu Phe Asp Leu Asn Asp Gln Tyr
        755                 760             765

Val Leu Asp Ala Gln Arg Lys Gly Asp Lys Leu Lys Phe Ala Asn His
    770             775             780

Ser Ala Lys Pro Asn Cys Tyr Ala Lys Val Met Phe Val Ala Gly Asp
785             790             795                         800

His Arg Val Gly Ile Phe Ala Asn Glu Arg Ile Glu Ala Ser Glu Glu
                805             810                 815

Leu Phe Tyr Asp Tyr Arg Tyr Gly Pro Asp Gln Ala Pro Val Trp Ala
            820             825             830

Arg Lys Pro Glu Gly Ser Lys Lys Asp Asp Ser Ala Ile Thr His Arg
        835             840             845

Arg Ala Arg Lys His Gln Ser His
850                 855
```